United States Patent [19]

Hasebe et al.

[11] Patent Number: 5,047,022

[45] Date of Patent: Sep. 10, 1991

[54] DEODORANT BEDDING

[76] Inventors: Kaoru Hasebe, 471, Komiya, Harima-cho; Naoki Minamide, 455-1, Komiya, Harima-cho; Seigo Higaki, 386, Honjo, Harima-cho, all of Kako-gun, Hyogo 675-01; Hirohusa Shirai, 2496, Nagase, Maruko-cho, Chiisagata-gun, Nagano 386-04; Kouichi Hukamachi, 18-5, Chuo, 5-chome, Ueda-shi, Nagano 386, all of Japan

[21] Appl. No.: 470,796

[22] Filed: Jan. 26, 1990

Related U.S. Application Data

[63] Continuation-in-part of Ser. No. 144,035, Aug. 7, 1987, abandoned.

[30] Foreign Application Priority Data

Dec. 24, 1985 [JP] Japan ............................... 60-289267

[51] Int. Cl.$^5$ ....................... A61F 13/15; A61F 13/20

[52] U.S. Cl. .................................... 604/359; 604/360; 604/375

[58] Field of Search ................ 604/360, 361, 375, 359

[56] References Cited

U.S. PATENT DOCUMENTS

| | | | |
|---|---|---|---|
| 2,693,439 | 11/1954 | Blanchard et al. | 604/370 |
| 3,923,645 | 12/1975 | Anderson, Jr. et al. | 208/206 |
| 3,952,347 | 4/1976 | Comerford et al. | |
| 4,048,097 | 9/1977 | Douglas | 252/431 N |
| 4,049,572 | 9/1977 | Douglas | 252/431 N |
| 4,212,852 | 4/1980 | Aibe et al. | 423/230 |
| 4,363,322 | 12/1982 | Anderson | 604/375 |
| 4,385,632 | 5/1983 | Oldehog | 604/360 |
| 4,390,018 | 6/1983 | Zukowski | |
| 4,413,996 | 11/1983 | Taylor | 604/382 |
| 4,515,761 | 5/1985 | Plotzker | 423/240 |
| 4,675,014 | 6/1987 | Sustmann et al. | 604/375 |
| 4,911,898 | 3/1990 | Hagiwara et al. | 604/360 |

FOREIGN PATENT DOCUMENTS

| | | |
|---|---|---|
| 2819933 | 11/1978 | Fed. Rep. of Germany . |
| 0133590 | 11/1978 | Japan . |
| 56-63355 | 5/1981 | Japan . |
| 0160963 | 8/1985 | Japan . |
| 0007000 | 1/1987 | Japan . |

OTHER PUBLICATIONS

Byoin-Setsubi, vol. 27, No. 6, pp. 571-577, Nov., 1985.

Int'l Search Report, Int'l. Appln. No. PCT/JP/00354-WO 87/03801.

*Primary Examiner*—Stephen C. Pellegrino
*Assistant Examiner*—Gary Jackson
*Attorney, Agent, or Firm*—Parkhurst, Wendel & Rossi

[57] ABSTRACT

Deodorant bedding of this invention comprises wadding having a first fiber retaining metal complex having oxidation-reduction power and a second fiber retaining metal ion. Therefore, foul smelling substances are oxidized by the metal complex and adsorbed by metal ion complex exchange reaction, and then the bedding will be deodorized.

4 Claims, 1 Drawing Sheet

DEODORANT BEDDING

CROSS-REFERENCE TO RELATED APPLICATIONS

This is a continuation-in-part of U.S. application Ser. No. 07/144,035, entitled "DEODORANT BEDDING", filed Aug. 7, 1987, now abandoned.

TECHNICAL FIELD

This invention relates to deodorant bedding, particularly suitable for persons suffering from incontinence, such as physically handicapped, bedridden and bedwetting persons.

BACKGROUND ART

Mattresses and quilts, which are commonly used for bedding, contain fibers which absorb humidity. The form of wadding is retained by the assistance of force from the intertwining fiber. This type bedding is often difficult to wash and, as a result, becomes impregnated with fetor after a long use. To reduce the accumulation of fetor, it is usual to dry the bedding occasionally. However, it is difficult to dry the bedding used by bedridden patients, resulting in the inevitable accumulation of fetor.

Heretofore, to prevent such accumulation of fetor, bedding wadded with activated charcoal has been proposed by Japanese Utility Model Provisional Publication No. 81667/82.

In circumstances where persons, such as physically handicapped, bedridden or bed-wetting persons (hereinafter simply called patients), experience incontinence, fetor penetrates into the bedding during long periods of medical treatment. When this occurs, an unpleasant odor is emitted from the bedding and spreads and stays in the room. Though the above-mentioned bedding wadded with activated charcoal is useful for reducing unpleasant odors to some extent, the effect does not last very long. A long deodorizing effect cannot be expected unless the activated charcoal is renewed frequently.

Not only does the room occupied by an incontinent patient for a long period of time become filled with more rank odor than the patient realizes, but also the foul smell soaks into the patient. It makes visitors and attendants feel unpleasant, and consequently the patient is shunned by them. His character becomes gradually so closed and dark as to cause an undesirable social influence.

DISCLOSURE OF THE INVENTION

The present invention provides a new type of deodorant bedding that is suitable for incontinent patients. It is especially effective for removing the smell of urine and other excreta, and has a long life for maintaining a deodorant effect.

The deodorant bedding of the present invention comprises tick wraps, wherein at least a part of a wadding fiber A retains more than 1% by weight of a metal complex having oxidation-reduction power, and a fiber B retains metal ions. These fibers develop a substantial deodorant effect on the smell of excreta for a long period of time with higher durability.

The deodorant component of fiber A comprises metal porphyrin, metal porphyrazine and their derivatives that have oxidation-reduction power. These materials are retained with fibrous components of wadding by physical contact or by chemical bonds to form a polymer metal complex. FIG. 1(*a*) shows the structural formula of metal porphyrin and its derivatives. FIG. 1(*b*) shows structural formula of metal porphyrazine. In both formulas, M is, e.g., Fe, Co, Mn, Ti, V, Ni, Cu, Zn, Mo, or W. Among these metals, Fe and Co are preferable from the viewpoint of deodorant effect.

X represents H or its substituent groups. The substituent groups include alkyl, substituted alkyl (e.g., chloromethyl), halogen, nitro, amino, azo, thiocyanate, nitryl, hydroxyl, alkoxyl, phenoxyl, sulfonate, sulfonyl chloride, sulfonamide, thiol, alkylsilicon, and vinyl, as well as alkaline salts of carboxyl and sulfonic groups. These are used singly or in a combination of more than two different groups. Especially, carboxyl, sulfonate, their alkaline salts, amino, halogen, or hydroxyl groups are preferably used.

The most preferable examples of the metal complex with oxidation-reduction power are cobalt-phthalocyanine octa-carboxylic acid, cobalt phthalocyanine tetracarboxylic acid, ironphthalocyanine octa-carboxylic acid or iron-phthalocyanine tetracarboxylic acid. The above-mentioned metal complexes may be used singly or in a combination of more than two different complexes.

The content of the metal complex in wadding is generally more than 1% by weight, although it depends on the type of metal complex used. The deodorant activity is enhanced with an increase in the content of metal complex. A small content of the metal complex makes it impossible to obtain a desired level and high durability of deodorant activity. There is an upper limit in the amount of metal complex retained with fiber A. Thus, the preferable content of the metal complex ranges from 1% to 20% by weight.

The preferable metal ion retained with fiber B is an ion of a transition metal, for example Cu, Fe, Co or Ni. Also, preferable ions of other metals include, for example, Ca, Ba or Mg. These metals may be used singly or in a combination of more than two different kinds of the above-mentioned metals. Although increasing the content of metal ion as high as possible is desirable, the content ranging from 0.1% to 20% by weight is preferable from the. viewpoint of cost, strength and keeping shape of the fiber as a retainer. The fibers retain the above-mentioned metal ions by physical contact with the fiber or by chemical bonding to polymers of the fiber. An example of the latter is a formed polymer metal complex such as inter-molecular chelate complex of polyvinyl alcohol with Cu ion or a complex of polyvinylamine with Fe ion, etc. Otherwise, compounds containing the above-mentioned metal ion may be retained by physical contact with the fiber or by chemical bond with polymers of the fiber.

The fiber retaining metal complex and the fiber retaining metal ion include regenerated cellulose fiber, hygroscopic synthetic fiber, porous fiber or porous hollow fiber. Especially, regenerated cellulose fiber having a primary swelling rate of 150% to 500% is preferable.

Foul smelling materials, such a hydrogen sulfide and mercaptan, etc., are oxidized and decomposed by the catalytic action of the metal complex having oxidation-reduction power, the materials being retained with fiber A which is at least a part of the wadding of bedding of this invention. This oxidation process proceeds by the metal coordinate bonding with porphyrin or the porphyrazine ring.

As an example, the oxidation process of mercaptan can be expressed by the following reaction formula:

$$2R—SH+2OH^- \rightarrow 2R—S^- + 2H_2O \quad (1)$$

$$2R—S^- + 2H_2O + O_2 \rightarrow R—S—S—R + H_2O_2 + 2OH^- \quad (2)$$

The thiolate anion, a reaction product of formula (1), together with oxygen, combines with porphyrin or porphylazine by coordinate bond to form an active state of a three-dimensional complex. The thiolate anion in coordination bond with porphyrin or porphylazine dimerizes through a thiyl-radical to a disulfide, as shown in formula (2). Then the disulfide is concealed within the fiber. The mercaptan is thus deodorized.

This reaction is very similar to biological enzymatic oxidization. The oxidation reactions by the aid of enzymes are all aerobic reactions, i.e., almost all of them are oxidation reactions by oxygen. The following are examples of oxidation of foul smelling materials by oxidizing enzymes.

| Enzymatic Reactions | Examples of Reaction Formulas |
|---|---|
| Oxidase type | 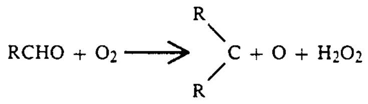 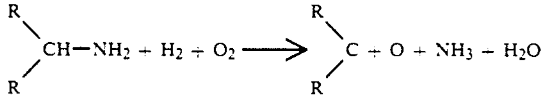 $H_2SO_3 + H_2O + O_2 \rightarrow H_2SO_4 + H_2O_2$ 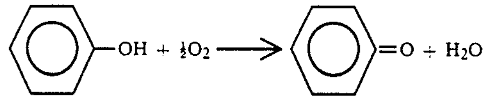 |
| Oxygenase type | Cleavage of double bond<br>Cleavage of indole nucleus<br>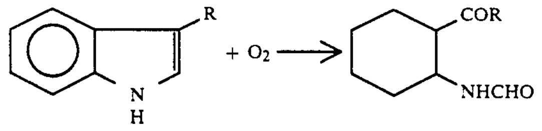 |

As mentioned above, there occur oxidation (deodorization) and sulfonation (water-solubilization, deodorization) of mercaptan compounds, quinonation (deodorization) of phenolic compounds, and cleavage of double bonds (deodorization) of the indole nucleus. The oxidation by the metal complex progresses at a rapid reaction rate with a high yield in the presence of a small quantity of moisture at room temperature.

For deodorization of foul smelling material comprising ammonia or various amines, the oxidizing decomposition by action of a metal complex having oxidation-reduction power is effective, and, furthermore, fiber B, which retains metal ion, can secure a more effective deodorization. The above-mentioned deodorant effect is in that the metal ion retained with fiber B forms a metal amine complex with ammonia or various amine compounds in the presence of moisture. For example, a reaction which forms a complex by adsorption of ammonia to Cu ion, is a complex exchange reaction between water molecules of hydrated Cu ion and ammonia molecules floating in air, as shown by the following formula:

$$[Cu(OH_2)_4]^{2+} + 4NH_3 \rightarrow [Cu(NH_3)_4]^{2+} + 4H_2O$$

This complex exchange reaction has a quick reaction rate and high degree of exchange, and the formed metal amine complex is adsorbed in a very stable condition.

Fiber A, retaining approximately 2% by weight of iron phthalocyanine polycarboxylate, was prepared by dipping rayon staple of approximately 240% in primary swelling and 31 mm in length into a aqueous solution of iron phthalocyanine polycarboxylate (concentration: 3 g/l pH: 12), and drying the staple. Also, fiber B, retaining approximately 2% by weight of copper ion, was prepared by dipping the same above-mentioned rayon staple into a aqueous solution of copper sulfate (concentration: 5 g/l) and drying the staple.

DESCRIPTION OF PREFERRED EMBODIMENTS

EXAMPLE 1

Figure 1A:
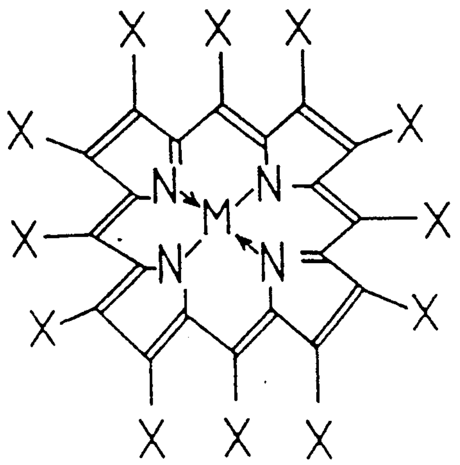
FIG. 1(*a*) shows a structural formula of metal porphyrin, and FIG. 1(*b*) shows that of metal porphyrazine.
Figure 1B:
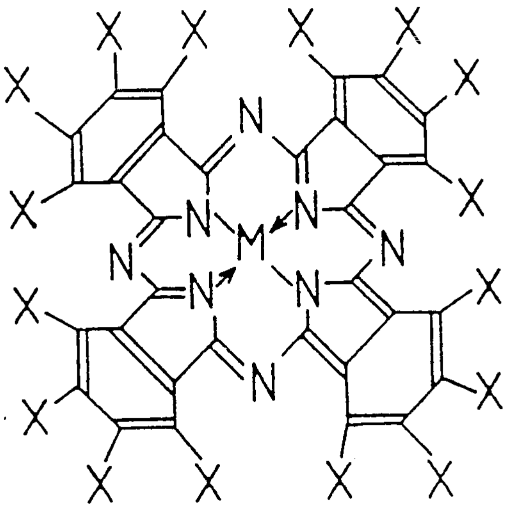

Fiber A, retaining approximately 2% by weight of iron phthalocyanine polycarboxylate, was prepared by dipping rayon staple of approximately 240% in primary swelling and 31 mm in length into an aqueous solution of iron phthalocyanine polycarboxylate (concentration: 3 g/l pH: 12), and drying the staple. Also, fiber B, retaining approximately 2% by weight of copper acetate, was prepared by dipping the same above-mentioned rayon staple into an aqueous solution of copper acetate (concentration 5 g/l) and drying the staple. Mixed fiber of 70% of the fiber A and 30% of the fiber B was also prepared. The mixed fiber thus is applicable as wadding for deodorant bedding of the present invention.

Fiber A, fiber B, and the mixed fiber were measured for deodorant efficiency as follows:

5 g of each fiber (A, B, and mixed A/B) was placed in a glass tube having 16 mm diameter and 100 mm length. An amount of air including 100 ppm of foul smelling material as shown in Table 1 below, was passed through each glass tube over a selected time interval, and then was put into an air-tight bag. The air in each bag was smelled by five monitors to judge the remaining odor. The result thereof is shown in Table 1. The value in Table 1 is an average value of the five monitors' evaluations. The five monitors assigned odor values as follows: (1) no odor as 0, (2) slight odor as I, (3) distinct odor as 2, and (4) extreme odor as 3.

As shown in Table 1, it was proved that the mixed fiber used for the deodorant bedding according to the present invention had excellent and unexpected deodorizing effects.

TABLE 1

| Foul smelling material | Lapsed Hour | Evaluated Value of Deodorizing Effect | | |
|---|---|---|---|---|
| | | Fiber A | Fiber B | Mixed Fiber |
| Hydrogen Sulfide Gas | 1 | 0 | 0 | 0 |
| | 5 | 0 | 2.8 | 0 |
| | 20 | 0 | 3 | 0 |
| | 30 | 2.6 | 3 | 0 |
| | 40 | 3 | 3 | 0 |
| | 50 | 3 | 3 | 2.8 |
| Methyl Mercaptan | 1 | 0 | 0 | 0 |
| | 5 | 0 | 0 | 0 |
| | 20 | 0 | 2.6 | 0 |
| | 30 | 2.2 | 2.8 | 0 |
| | 40 | 2.8 | 3 | 2.6 |
| | 50 | 3 | 3 | 3 |
| Ammonia | 1 | 0 | 0 | 0 |
| | 5 | 0 | 0 | 0 |
| | 20 | 0 | 0 | 0 |
| | 30 | 0 | 2.8 | 0 |
| | 40 | 3 | 3 | 0 |
| | 50 | 3 | 3 | 0 |
| Skatole | 1 | 0 | 0 | 0 |
| | 5 | 0 | 0 | 0 |
| | 20 | 0 | 2.2 | 0 |
| | 30 | 0 | 3 | 0 |
| | 40 | 3 | 3 | 0 |
| | 50 | 3 | 3 | 0 |

In addition, three types of bedding materials were prepared. Bedding A was prepared from waddings of 50% fiber A and 50% of commercially available polyester fiber. Bedding B was prepared from waddings of 50% fiber B and 50% of commercially available polyester fiber. Bedding C was prepared according to the present invention from mixed waddings of 25% of fiber A, 25% of fiber B, and commercially available polyester fiber. Each bedding material was formed into a set including a mattress and a quilt prepared by wrapping 5 kg of the waddings with tick of good air permeability. The bedding materials A, B, and C were then used by bedridden and incontinent patients for a long time.

Bedding materials A, B, and C were smelled by monitors to detect the odor of excretas at stated periods. The results of the judgments are shown in Table 2.

TABLE 2

| Time period | Judgment of Odor | | |
|---|---|---|---|
| | Bedding A | Bedding B | Bedding C |
| 1 month | no odor | no odor | no odor |
| 3 months | no odor | slight odor | no odor |
| 6 months | no odor | extreme odor | no odor |
| 1 year | no odor | | no odor |
| 2 years | slight odor | | no odor |
| 3 years | extreme odor | | no odor |

EXAMPLE 2

Mattresses of about 3 cm in apparent thickness were made by wrapping with tick having good air permeability, the wadding arranged in layering 65% of fiber A and 35% of fiber B which were prepared by the method described in Example 1. The mattresses were used by children of enuresis. Even after six months of repeated use, drying every time after wetting by urine, the mattresses emitted little foul smell.

EXAMPLE 3

Fiber B, retaining approximately 3% by weight of cobalt chloride, was prepared by dipping rayon staple into aqueous solution of cobalt chloride (concentration: 10 g/l) and drying the staple. Mattresses of about 3 cm in apparent thickness were made by wrapping with tick having a good air permeability, the wadding arranged in layering 65% of fiber A prepared by the method described in the above Example 1 and 35% of fiber B of this example. The result of the test was just the same as that of Example 2.

EXAMPLE 4

Fiber B, retaining approximately 3% by weight of ferrous acetate, was prepared by dipping rayon staple into aqueous solution of ferrous acetate (concentration: 20 g/l) and drying the staple. Mattresses of about 3 cm in apparent thickness were made by wrapping with tick having a good air permeability, the wadding arranged in layering 65% of fiber A prepared by the method described in the above Example 1 and 35% of fiber B of this example. The result of the test was just the same as that of Example 2.

INDUSTRIAL APPLICABILITY

In the deodorant bedding of this invention as described above, the wadding of fiber A, which retains metal complex having oxidation-reduction power, and fiber B, which retains metal ion having adsorption power, is wrapped with tick.

Therefore, mercaptan and aldehyde, etc., are oxidized by fiber A, indole, etc., are cleavaged by fiber A and ammonia and amine, etc., adsorbed by fiber B so that foul smell of urine and sweat are removed. The deodorizing power of the fibers lasts over a long term. The bedding of this invention can be made by the method described in the above examples and others. The feature of the bedding of this invention is particularly effective for long-term bedridden patients.

The foregoing description has been directed to particular embodiments of the present invention in order to comply with the requirements of the United States patent statutes. It will be apparent to those skilled in this art, however, that many modifications and changes in the invention set forth above will be possible without departing from the spirit and scope of the invention. It is intended that the following claims be interpreted to embrace all such modifications and changes as will be apparent to those of ordinary skill in the above technology.

What is claimed is:

1. A deodorant bedding comprising wadding and tick, said wadding comprising a mixture consisting of (1) about 35% by weight of a rayon staple fiber having a swelling rate of about 240% and which contains about 2% by weight of iron phthalocyanine polycarboxylate, (2) about 35% by weight of a rayon staple fiber having a swelling rate of about 240% and which contains about 2% to about 5% by weight of a compound selected from the group consisting of copper acetate, cobalt sulfate, and ferrous acetate, and (3) about 30% by weight of a polyester fiber.

2. A deodorant bedding comprising wadding and tick, said wadding arranged in layering of about 65% by weight of a first rayon staple fiber having a swelling rate of about 240% and which contains about 2% by weight of iron phthalocyanine polycarboxylate and about 35% by weight of a second rayon staple fiber having a swelling rate of about 240% and which contains about 2% to about 5% of a compound selected from the group consisting of copper acetate, cobalt sulfate, and ferrous acetate.

3. The deodorant bedding of claim 2, wherein said second rayon staple fiber contains about 3% by weight of cobalt sulfate.

4. The deodorant bedding of claim 2, wherein said second rayon staple fiber contains about 5% by weight of ferrous acetate.

* * * * *